(12) United States Patent
Kitano et al.

(10) Patent No.: US 8,421,470 B2
(45) Date of Patent: Apr. 16, 2013

(54) DISCHARGE IONIZATION CURRENT DETECTOR

(75) Inventors: Katsuhisa Kitano, Ibaraki (JP); Satoshi Hamaguchi, Kyoto (JP); Kei Shinada, Uji (JP)

(73) Assignees: Osaka University, Osaka (JP); Shimadzu Corporation, Kyoto (JP)

( * ) Notice: Subject to any disclaimer, the term of this patent is extended or adjusted under 35 U.S.C. 154(b) by 243 days.

(21) Appl. No.: 12/934,063

(22) PCT Filed: Mar. 19, 2009

(86) PCT No.: PCT/JP2009/001250
§ 371 (c)(1), (2), (4) Date: Sep. 22, 2010

(87) PCT Pub. No.: WO2009/119050
PCT Pub. Date: Oct. 1, 2009

(65) Prior Publication Data
US 2011/0018546 A1  Jan. 27, 2011

(30) Foreign Application Priority Data

Mar. 25, 2008 (JP) ................ 2008-076917
Sep. 2, 2008 (JP) ................ 2008-224483

(51) Int. Cl.
*G01N 27/62* (2006.01)
(52) U.S. Cl.
USPC ........................................ 324/464
(58) Field of Classification Search ........... 324/464
See application file for complete search history.

(56) References Cited

U.S. PATENT DOCUMENTS 4,466,943 A * 8/1984 Murase et al. ............... 422/91
4,641,970 A * 2/1987 Gustafson et al. ........... 356/472
(Continued)

FOREIGN PATENT DOCUMENTS
JP 05-005704 1/1993

OTHER PUBLICATIONS

Chinese language office action dated Apr. 25, 2012 and its partial English language translation issued in corresponding Chinese application 200980110438.2.

(Continued)

*Primary Examiner* — Patrick Assouad
*Assistant Examiner* — Demetrius Pretlow
(74) *Attorney, Agent, or Firm* — DLA Piper LLP (US)

(57) ABSTRACT

A low-frequency high AC voltage from an excitation voltage power source (14) is applied between one electrode (8) and two other electrodes (9A and 9B) to generate a low-frequency AC-excited dielectric barrier discharge within a gas passage (3), thereby creating atmospheric pressure non-equilibrium micro-plasma. A sample gas is mixed with hydrogen inside the passage of a nozzle (51), and further mixed with air outside an exit port (53) to burn, forming a hydrogen flame (57). Then, the sample gas reaches an ionization area (56), where the sample components are ionized due to the effect of light emitted from the plasma. Meanwhile, water molecules generated in the hydrogen flame (57) are supplied into the ionization area (56), whereby some of the sample-molecule ions are hydrated while the others undergo a reaction to form a hydroxonium ion. These kinds of hydrated ions have long lifetimes and barely become extinct halfway, so that they can efficiently reach a detection electrode (13) and be detected as ion current. As a result, the detection sensitivity is improved and the dynamic range is enhanced.

15 Claims, 9 Drawing Sheets

U.S. PATENT DOCUMENTS

| | | | | |
|---|---|---|---|---|
| 5,116,764 | A | * | 5/1992 | Annino et al. ............... 436/161 |
| 5,153,673 | A | * | 10/1992 | Amirav ........................ 356/315 |
| 5,394,092 | A | | 2/1995 | Wentworth et al. ........... 324/464 |
| 5,432,095 | A | * | 7/1995 | Forsberg ....................... 436/154 |
| 5,576,626 | A | * | 11/1996 | Lo ................................ 324/464 |
| 5,892,364 | A | * | 4/1999 | Monagle ...................... 324/464 |
| 6,842,008 | B2 | | 1/2005 | Stearns et al. ................ 324/464 |
| 7,046,012 | B2 | * | 5/2006 | Dean et al. ................... 324/459 |
| 7,408,360 | B2 | * | 8/2008 | Sheverev ...................... 324/464 |
| 2004/0178800 | A1 | | 9/2004 | Stearns et al. ................ 324/464 |
| 2004/0245993 | A1 | * | 12/2004 | Bonne ........................... 324/464 |
| 2007/0289359 | A1 | * | 12/2007 | Shannon et al. ............... 73/23.2 |
| 2008/0116139 | A1 | * | 5/2008 | Liu et al. ...................... 210/656 |

OTHER PUBLICATIONS

A. M. Myres et al., "Energy and mass-resolved detection of neutral and ion species using modulated-pole-bias quadrupole mass spectroscopy" J. Vac. Sci. Techno Lab(3). May/Jun. 1990, pp. 1668-1672.

M. Teschke et al., "High-speed photographs of a dielectric barrier atmospheric pressure plasma jet", IEEE Transactions on Plasma Science, vol. 33, No. 3, Apr. 2005, pp. 310-311.

Ronda Gras et al., "Gas chromatographic applications with the dielectric barrier discharge detector", Journal of Chromatographic Science, vol. 44, Feb. 2006, pp.

Peter Boček et al., "Flame Ionisation Detection", Chromatograph Rev., 15, 1971, pp. 111-150.

Kazuo Nishikawa et al., "Airborne Viruses Inactivation with Cluster Ions Generated in a Discharge Plasma", Sharp Gihou, No. 86, Aug. 2003, pp. 10-15.

D. Liu et al., "Diagnosis of dielectric barrier discharge $CH_4$ plasma for diamond-like carbon film deposition", Diamond and Related Materials, vol. 11, Issue 8, Mar. 18, 2002, pp. 1491-1495.

Translation of the International Preliminary Report on Patentability.

* cited by examiner

VOLTAGE-CURRENT CURVE FOR AC BIAS VOLTAGE SET AT 0.01[Hz]

VOLTAGE-CURRENT CURVE FOR AC BIAS VOLTAGE SET AT 1[kHz]

DISCHARGE IONIZATION CURRENT DETECTOR

CROSS-REFERENCE TO RELATED APPLICATIONS

This application is a national stage of international application No. PCT/JP2009/001250, filed on Mar. 19, 2009, and claims the benefit of priority under 35 USC 119 to Japanese Patent Application No. 2008-076917, filed Mar. 25, 2008 and Japanese Patent Application No. 2008-224483, filed Sep. 2, 2008, the entire contents of which are incorporated herein by reference.

TECHNICAL FIELD

The present invention relates to a discharge ionization current detector primarily suitable as a detector for a gas chromatograph (GC).

BACKGROUND ART

As the detector for a gas chromatograph, various types of detectors have conventionally been proposed and practically applied, such as a thermal conductivity detector (TCD), electron capture detector (ECD), flame ionization detector (FID), flame photometric detector (FPD) and flame thermionic detector (FTD). Among those detectors, the FID is most widely used, particularly for the purpose of detecting organic substances. The FID is a device that ionizes sample components in a sample gas by hydrogen flame and detects the resultant ion current. It can attain a high dynamic range of approximately six-digit levels.

However, the FID has the following drawbacks: (1) Its ionization efficiency is low, so that its minimum detectable amount is not sufficiently low. (2) Its ionization efficiency for alcohols, aromatic substances and chlorine substances is low. (3) It requires hydrogen, which is a highly hazardous substance; therefore, an explosion-proof apparatus or similar kind of special equipment must be provided, which makes the entire system more difficult to operate.

On the other hand, as a detector capable of detecting various compounds from inorganic substances to low-boiling organic compounds, a pulsed discharge detector (PDD) has conventionally been known (for example, refer to Patent Document 1) and practically used (for example, refer to Non-Patent Document 1). In the pulsed discharge detector, the molecules of helium or another substance are excited by a high-voltage pulsed discharge. When those molecules return from the excited state to the ground state, they generate an optical energy. This optical energy is utilized to ionize a molecule to be analyzed. An ion current produced by the generated ions is detected to obtain a detection signal corresponding to the amount (concentration) of the molecule to be analyzed.

In most cases, the pulsed discharge detector can attain higher ionization efficiencies than the flame ionization detector (FID). For example, the ionization efficiency of the FID for propane is as low as 0.0005 [%], whereas the pulsed discharge detector has achieved a level as high as 0.07 [%]. Despite this advantage, the dynamic range of the pulsed discharge detector is not as high as that of the FID; the fact is that the former is one or more digits lower than the latter. This is one of the reasons why the pulsed discharge detector is not as widely used as the FID.

Patent Document 1: Specification of U.S. Pat. No. 5,394,092

Patent Document 2: Specification of U.S. Pat. No. 5,892,364

Non-Patent Document 1: "Muki-Gas Bunseki Ha ppb No Ryouiki He; PPD Koukando Bunseki Shisutemu (For Inorganic Gas Analysis at ppb Levels; PPD High-Sensitivity Analysis System)", [online], Shimadzu Corporation, [searched on Feb. 29, 2008], Internet <URL: http://www.an-.shimadzu.co.jp/products/gc/pdd.htm>

Non-Patent Document 2: M. Teschke et al., "High-Speed Photographs of a Dielectric Barrier Atmospheric Pressure Plasma Jet", *IEEE Transaction on Plasma Science*, Vol. 33, No, 2, April 2005, pp. 310-311

Non-Patent Document 3: R. Gras et al., "Gas Chromatographic Applications with the Dielectric Barrier Discharge Detector", *Journal of Chromatographic Science*, Vol. 44, February 2006

Non-Patent Document 4: P. Bocek et al., "Flame Ionisation Detection", *Chromatographic Reviews*, 15(1971), pp. 111-150

Non-Patent Document 5: K. Nishikawa and H. Nojima, "Airborne Viruses inactivation with Cluster Ions Generated in a Discharge Plasma", *Sharp Gihou*, No. 86, August 2003, pp. 10-15

Non-Patent Document 6: The Institute of Electrostatics Japan, ed., *Seidenki Hando-Bukku (Electrostatics Handbook)*, Ohm-sha (Tokyo), Nov. 2006, pp. 213-214

DISCLOSURE OF THE INVENTION

Problem to be Solved by the Invention

Although the limiting factors for the dynamic range of the conventional pulsed discharge detector have not yet been definitely clarified, one possible reason is as follows. In the conventional pulsed discharge detectors, plasma is created by an electric discharge, which is generated by applying a pulsed high-voltage with a short duration between an array of electrodes arranged at small intervals of a few mm or shorter. This is an improved version of a DC discharge; the application of the pulsed voltage is intended to suppress the heating of the electrodes and the destabilization of the plasma, which occur in the case of the DC discharge.

However, the use of the pulsed voltage results in a periodic fluctuation of the plasma according to the transition of the voltage states, such as the rise, peak and fall of the pulsed voltage, and this fluctuation of the plasma directly causes a periodic change of the ionization. That is to say, since an efficient excitation can occur only periodically, the average excitation efficiency decreases, causing the plasma to be unstable. This is one probable reason for the destabilization of the ionization. The periodic fluctuation in the plasma state may also cause a background noise. Due to these reasons, the S/N ratio of the detection signal of the conventional pulsed discharge detector cannot be adequately high. This is the most probable limiting factor for the dynamic range.

One possible method for steadily maintaining the plasma state is to use a radio-frequency discharge in place of the DC discharge. However, this will increase the temperature of the plasma and may possibly cause various problems. For example, the thermions or the like created due to an increase in the temperature of the discharge electrodes or other elements may affect the plasma and destabilize the plasma state. Another problem is that the detector must be designed to have a heat-resistant configuration and structure, which will cause a significant increase in cost.

In view of these problems, Patent Document 2, Non-Patent Document 3 and other documents disclose a discharge ionization current detector using a low-frequency AC-excited dielectric barrier discharge to create plasma. (Detailed reports on the low-frequency alternating excitation dielectric barrier discharge are available in Non-Patent Document 2 or other documents.) The plasma created by the low-frequency alternating excitation dielectric barrier discharge is a non-equilibrium atmospheric pressure plasma, which does not become hot so easily as the plasma created by the radio-frequency discharge. Furthermore, the periodic fluctuation of the plasma, which occurs due to the transition of the voltage application state if the plasma is created by the pulsed high-voltage excitation, is prevented, so that a stable and steady plasma state can be easily obtained. However, a study by the present inventors have revealed that, even with the aforementioned discharge detector using the low-frequency alternating excitation dielectric barrier discharge, it is difficult to achieve a dynamic range comparable or superior to that of the flame ionization detector.

The present invention has been developed to solve the previously described problems. Its main objective is to provide a discharge ionization current detector capable of improving the analysis sensitivity and accuracy by ensuring a dynamic range wider than those of the conventional discharge detector using a low-frequency AC-excited dielectric barrier discharge as well as those of the conventional pulsed discharge detectors.

Means for Solving the Problems

In a discharge ionization current detector, the main excitation source for the ionization of the molecules of a gaseous sample is the optical energy from the electric discharge or plasma. The sample molecules are ionized by the optical energy, and the resultant sample-molecule ions move to an ion-current detection electrode to be reflected in an ion current. However, an ion of a gas sample molecule normally has an extremely short life, which is in the neighborhood of microseconds, and a high percentage of those ions become extinct before reaching the ion-current detection electrode. Therefore, the usage efficiency of the produced ions (i.e. the percentage of ions that reach the ion-current detection electrode) is rather low, so that the detection sensitivity barely increases even if the ionization efficiency is improved. This is probably one of the factors suppressing the dynamic range.

On the other hand, it is known that the flame ionization detector produces various ions and radicals in a hydrogen flame by the burning of hydrogen and a sample (refer to Non-Patent Document 4). The main reaction relating to the ion current is the reaction between oxygen and a hydrocarbon radical generated from the sample in the hydrogen flame, as shown in the following reaction formula (1):

$$CH + O \rightarrow CHO^+ + e^- \qquad (1)$$

The CHO$^+$ ion generated by this reaction is unstable and immediately reacts with a water molecule generated in the hydrogen flame, to produce a hydroxonium ion (or oxonium ion) as shown in the following reaction formula (2):

$$CHO^+ + H_2O \rightarrow H_3O^+ + CO \qquad (2)$$

The hydroxonium ion is a kind of hydrated ion. Normally, hydrated ions have longer lifetimes than non-hydrated ions. For example, it is known that a measurement of ions generated by an electric discharge in air shows that most of those ions are hydrated ions (refer to Non-Patent Documents 5 and 6). This fact demonstrates that the hydrated ions have longer lifetimes. A majority of the ion current detected by the flame ionization detector is constituted by such hydrated ions, and it is possible that the relatively wide dynamic range of this detector is due to the long life of the hydrated ions.

In view of these points, the present inventors have come up with the idea of applying the previously described ion-current detection mechanism of the flame ionization detector in the discharge ionization current detector using a low-frequency AC-excited dielectric barrier discharge, to lengthen the lifetime of the ions generated from a sample component and thereby enhance the efficiency of the ions' reaching the ion-current detection electrode so that the dynamic range will be improved.

The first aspect of the present invention aimed at solving the aforementioned problems is a discharge ionization current detector having a discharge generation means for generating plasma from a predetermined gas by electric discharge and a current detection means with a detection electrode for detecting an ion current due to a gaseous sample component ionized by irradiation with light emitted from the plasma generated by the discharge generation means, which is characterized by including:

a flame formation means for forming a hydrogen flame by burning a mixture of hydrogen and either air or oxygen so as to supply a water molecule into an ionization area where the ionization of the sample component due to the irradiation with light occurs or a space between the ionization area and the detection electrode.

In the discharge ionization current detector according to the first aspect of the present invention, when the flame formation means forms a hydrogen flame by burning a mixture of hydrogen and either air or oxygen, the water molecules resulting from the burning reaction are supplied into an area where the sample-molecule ions produced by the irradiation with light abundantly exist. When the water molecules combine with a sample-molecule ion, the sample-molecule ion becomes hydrated and forms a hydrated ion (i.e. the sample molecule ion becomes surrounded by the water molecules). Alternatively, the water molecule may react with the sample-molecule ion to form a hydroxonium ion. These kinds of hydrated ions have longer lifetimes than the original gaseous sample-molecule ion and will be scarcely dissipated while moving. Thus, a higher percentage of those ions will reach the detection electrode and be reflected in the ion current.

Thus, in the discharge ionization current detector according to the first aspect of the present invention, the ionization of the sample component is caused by the electric discharge itself or the action of the light emitted from the plasma. Therefore, not only organic compounds but also inorganic substances can be efficiently ionized. The generated various ions originating from the sample will be hydrated by the action of the water molecules supplied from the hydrogen flame. The hydrated ions have longer lifetimes and can efficiently reach the detection electrode. Thus, while making full use of the advantages of the discharge ionization current detector, i.e. the detection capability for a wide variety of substances and the high ionization efficiency, the present technique enables the generated ions to be effectively reflected in the ion current. As a result, the detection sensitivity is improved and the dynamic range is thereby widened.

As a first mode of the discharge ionization current detector according to the first aspect of the present invention, the flame formation means may be placed so that the hydrogen flame is formed in an upstream portion of a sample-gas stream containing the sample component supplied into the ionization area.

As a second mode of the discharge ionization current detector according to the first aspect of the present invention, the flame formation means may be placed so that the hydrogen flame is formed between the ionization area and the detection electrode, in a sample-gas stream supplied so that the sample gas flows via the ionization area to the detection electrode.

As a third mode of the discharge ionization current detector according to the first aspect of the present invention, the flame formation means may be placed so that the hydrogen flame is formed on the upstream side of the ionization area, in a plasma-gas stream supplied so that the plasma gas flows via a plasma creation area, where the plasma is generated by electric discharge caused by the discharge generation means, to the ionization area.

In any of the first through third modes, the water molecules produced in the hydrogen flame are carried by a gas stream to an area where the ions originating from the sample component abundantly exist. Therefore, the water molecules have a high probability of contact with the sample-molecule ions, so that the generation of hydroxonium ions by the hydration or reaction of the sample-molecule ion can occur more efficiently.

Particularly, the second mode is advantageous to improving the efficiency in the hydration of sample-molecule ions or the generation of hydroxonium ions since the sample-molecule ions directly pass through the hydrogen flame and hence have an even higher chance of contact with water molecules.

In the first and second modes, since the sample gas passes through a hydrogen flame, the generation of sample-molecule ions takes place not only due to the electric discharge and the action of the light emitted from the plasma, but also due to the combustion of the sample component in the hydrogen flame. Therefore, the ion production efficiency itself is also improved, whereby the dynamic range is further enhanced.

In the discharge ionization current detector according to the first aspect of the present invention, the discharge generation means may preferably include:

a pair of discharge electrodes, at least one of the discharge electrodes having a surface covered with a dielectric material; and a voltage application means for applying an AC voltage having a frequency within a range from 1 [kHz] to 100 [kHz] to the discharge electrodes.

The aforementioned predetermined gas, i.e. the plasma gas, may be any gas selected from the group consisting of helium, argon, nitrogen, neon, xenon, and any mixture of these gases. As the dielectric material covering the surface of the discharge electrode, silica glass may be preferably used. The use of silica glass contributes to the stabilization of the plasma since silica glass is both thermally and chemically stable and barely causes outgassing.

In the previously described configuration, a non-equilibrium atmospheric pressure micro plasma is generated by a low-frequency AC-excited dielectric barrier discharge. By the action of the excitation light or excited species emitted from this plasma, an objective sample component is ionized, and a resultant ion current is detected by the current detection means. Since at least one of the discharge electrodes has its surface covered with a dielectric material, the metallic area exposed to the plasma is smaller than in the case of the conventional pulsed discharge ionization current detector. When exposed to plasma, the metallic surface would emit secondary electrons; these electrons would affect the plasma and change the state of the plasma. Furthermore, the plasma would contaminate the metallic surface, and the plasma state would vary according to the increasing degree of contamination. Due to these factors, the plasma would become more unstable as the exposed area of the metallic surface increases. In the case of the dielectric barrier discharge electrode in which the metallic surface is covered with a dielectric material, the area of the metallic surface exposed to the plasma is reduced, so that the plasma becomes more stable than in the case where it is generated by a conventional method using a normal pulsed discharge.

In the non-equilibrium atmospheric pressure plasma generated by a dielectric plasma discharge, the plasma barely reaches high temperatures since the power supply is temporarily discontinued before a sudden heating of the plasma initiates. Particularly, the plasma temperature is maintained low when the power supply is performed at low frequency. Therefore, the temperature rise of the portions exposed to the plasma is small and the emission of thermions or impurity gases from these portions is reduced. The thermions and impurity gases constitute destabilizing factors of the plasma state. Removing these factors improves the stability of the plasma.

Other discharging methods, such as the high frequency AC excitation or ultra-short pulsed high-voltage excitation, are accompanied by heat generation and hence require cooling the discharge electrodes. The cooling of the discharge electrodes is normally achieved by supplying a flow of plasma generation gas. To ensure an appropriate amount of heat release, it is necessary to continue the gas supply at a flow rate equal to or higher than a predetermined level. A failure to ensure the required gas flow will cause overheating of the discharge electrodes, which may be eventually damaged or broken. By contrast, the low-frequency AC-excited dielectric barrier discharge hardly generates heat. Therefore, even when the gas flow is not present, the discharge will be maintained in a normal way and the discharge electrodes will never be damaged. Accordingly, for example, if the gas supply is discontinued or its flow rate is decreased due to some abnormality, the apparatus will not undergo any damage. Thus, a highly reliable fail-safe system is realized.

Furthermore, unlike the plasma generated by a pulsed high-voltage excitation, the non-equilibrium atmospheric pressure plasma generated by low-frequency AC excitation is free from the periodic fluctuation due to the transition of the state of the applied voltage. Thus, a virtually steady state of plasma is obtained.

In the discharge ionization current detector having the previously described configuration, it is possible to adopt either a both-side dielectric barrier discharge structure in which the surfaces of both of the paired discharge electrodes are covered with the dielectric material, or a single-side dielectric barrier discharge structure in which the surface of only one discharge electrode is covered with the dielectric material. In the case of the both-side dielectric barrier discharge structure, the electric discharge itself is highly stable, so that the thereby created plasma is also stable. Therefore, due to the aforementioned reason, this structure is advantageous to reducing the noise to achieve higher S/N ratios and wider dynamic ranges.

On the other hand, the single-side dielectric barrier discharge structure supplies a greater amount of electrons to the plasma than the double-side dielectric barrier discharge structure, so that the plasma energy will rise to higher levels. This causes an increase in the emission of the excitation light and excited species, whereby the ionization performance can be improved. Therefore, for example, even when a gas has a high ionization potential and hence is difficult to be ionized (e.g. $N_2$ or $CF_4$), the ionization can be efficiently performed to achieve a sensitivity improvement. In the case of the single-side dielectric barrier discharge structure, when the surface of the electrode closer to the ion-current detection electrode is made of a metal not covered with the dielectric material, the electrons, ions and other charged particles in the plasma are prevented from directly impinging on the ion-current detection electrode, whereby the noises due to those charged particles are reduced and the S/N ratio is improved.

A discharge ionization current detector using a low-frequency AC excited dielectric barrier discharge cannot achieve an adequately high ionization efficiency when the frequency of the AC voltage applied to the discharge electrode is lower than 1 [kHz], On the other hand, increasing the frequency to a level higher than 100 [kHz] not only improves the ionization efficiency but also significantly increases the plasma temperature. This causes a temperature rise of the portions exposed to the plasma, and the previously described problem due to the temperature rise will be noticeable. Accordingly, a frequency range of 1 [kHz] to 100 [kHz] is specified. However, to maintain the plasma at low temperatures while ensuring a sufficient ionization performance, it is preferable to set the AC voltage within a range from 5 [kHz] to 50 [kHz]. Selecting this frequency range will particularly show the advantageous effects of the use of the low-frequency AC-excited dielectric barrier discharge.

In the discharge ionization current detector utilizing the low-frequency AC-excited dielectric barrier discharge in the previously described manner, it is preferable to provide an auxiliary electrode between the discharge electrode and the ion-current detection electrode, and to connect the auxiliary electrode to the ground or a reference potential point. In this configuration, the electrons, ions and other charged particles generated by plasma will be captured by the auxiliary electrode, thereby being prevented from directly impinging on the ion-current detection electrode. This will further reduce the noise and improve the S/N ratio. This effect of the auxiliary electrode is the same as the effect obtained in the previously described case of the single-side dielectric barrier discharge structure in which the surface of the electrode closer to the ion-current detection electrode is made of a metal not covered with the dielectric material. Therefore, the present configuration can exhibit particularly noticeable effects when applied to the double-side dielectric barrier electrode structure rather than the single-side dielectric barrier electrode structure.

In the discharge ionization current detector according to the first aspect of the present invention, the current detection means may preferably include a pair of detection electrodes, a bias-voltage application means for applying an AC bias voltage having a predetermined frequency to one of the detection electrodes, and a lock-in detection means for performing a lock-in detection of a signal obtained from the other detection electrode with respect to a reference signal having the same frequency as that of the AC bias voltage.

That is, positive ions or electrons originating from sample components are oscillated by using an AC voltage as the bias voltage, and an AC current component resulting from this oscillation is detected. By such a lock-in detection, the detection signal is limited to the frequency component of the AC bias voltage, excluding the other frequency components. This operation reduces various kinds of disturbing noises, such as the electromagnetic noise flying into a signal line or similar element or a noise due to a temperature fluctuation (e.g. a thermo-electromotive force). Particularly, the frequency band limitation by the lock-in detection is considerably effective in removing low-frequency noises (lower than 10 [Hz]), such as the noise due to the temperature fluctuation. Such a low-frequency noise has a frequency that approximately equals that of the original signal component and hence is difficult to remove by means of a filter or similar devices.

In the lock-in detection as described previously, if the parasite capacitance of an electrode or signal cable is driven by the AC bias voltage, the electrode or cable will generate unnecessary current signals. However, the current due to the parasite capacitance has an approximately 90-degree phase difference with respect to the voltage signal, whereas the phase difference of the signal component due to the ion current originating from the sample components is approximately zero. Therefore, it is possible to remove the current component due to the parasite capacitance and exactly detect only the ion-current signal by setting the detection phase difference of the lock-in detection means so that the lock-in detection output becomes zero when no plasma is generated by the discharge generation means.

As explained previously, the lock-in detection can reduce disturbing noises associated with the detection of the ion current. This technique can also be applied to a discharge ionization current detector utilizing a low-frequency AC-excited dielectric barrier discharge that does not use the flame formation means.

Thus, a discharge ionization current detector according to the second aspect of the present invention is a discharge ionization current detector including a discharge generation means for generating plasma from a predetermined gas by electric discharge and a current detection means for detecting an ion current due to a gaseous sample component ionized by an action of the generated plasma, which is characterized in that:

the discharge generation means includes a pair of discharge electrodes, at least one of the discharge electrodes having a surface covered with a dielectric material, and a voltage application means for applying an AC voltage having a frequency within a range from 1 [kHz] to 100 [kHz] to the discharge electrodes; and the electric current detection means includes a pair of detection electrodes, a bias voltage application means for applying an AC bias voltage having a predetermined frequency to one of the detection electrodes, and a lock-in detection means for performing a lock-in detection of a signal obtained from the other detection electrode with respect to a reference signal having the same frequency as that of the AC bias voltage.

In the discharge ionization current detector according to the second aspect of the present invention, it is preferable to set a detection phase difference of the lock-in detection means so that the detection output obtained by the lock-in detection means becomes zero when no plasma is generated by the plasma generation means.

EFFECTS OF THE INVENTION

In the discharge ionization current detector according to the first aspect of the present invention, the ions generated from a sample component by an electric discharge itself or by the action of the light emitted from plasma generated by the electric discharge will be efficiently reflected in the ion current, so that the detection sensitivity improves and the dynamic range widens. Furthermore, when the hydrogen flame is placed in a sample-gas stream, the ionization of the sample component also occurs due to the flame, which additionally improves the ion generation efficiency. This is further advantageous to the widening of the dynamic range.

When a low-frequency AC-excited dielectric barrier discharge is used, the plasma for ionizing the sample component maintains a stable and steady state, so that the ionization of the sample components also occurs in a stable manner. The noise level is also lowered by reducing the amount of secondary electrons and thermions emitted from the discharge electrode or other elements; those electrons and thermions can cause a noise not only by affecting the state of the plasma but also, more directly, by flying into the ion-current detection electrode. As a result, the S/N ratio of the detected ion current is improved, so that the dynamic range can be widened.

In the discharge ionization detector according to the second aspect of the present invention, the disturbing noises in low-frequency ranges are particularly reduced. Accordingly, the ion current originating from a sample component can be measured with high S/N ratios, so that the dynamic range can be widened.

EXPLANATION OF NUMERALS 100A, 100B, 200A, 200B, 200C, 300 . . . Discharge Ionization Current Detector
2, 50 . . . Detection Cell
3 . . . Gas Passage
4 . . . Gas Supply Port
5 . . . Gas Discharge Port
10, 11 . . . Dielectric Coating Layer
12 . . . Ion-Current Detection Electrode (Bias-Voltage Application Electrode)
13 . . . Ion-Current Detection Electrode (Ion-Current Collection Electrode)
14 . . . Excitation High-Voltage Power Source
15 . . . Bias DC Power Source
16 . . . Current Amplifier
17 . . . Ion-Current Detection Unit
18 . . . Electric Discharge
21 . . . Cylindrical Pipe
22 . . . Insulation Pipe
23 . . . Merging Passage
25 . . . Electrically Conductive Electrode
30 . . . Branch Exhaust Pipe
31 . . . Discharge Port
40 . . . Ion-Current Detection Unit
41 . . . Lock-in Amplifier
42 . . . Current Amplifier
43 . . . Power Amplifier
51 . . . Hydrogen Flame Formation Nozzle
52 . . . Hydrogen Supply Pipe
53 . . . Exit Port
54 . . . Combustion Air Supply Pipe
55 . . . Discharge Pipe
56 . . . Ionization Area
57 . . . Hydrogen Flame
58 . . . Sample-Gas Introduction Pipe
6 . . . Sample-Gas Introduction Passage
7 . . . Sample-Gas Supply Port
8, 9, 9A, 9B . . . Plasma Generation Electrode

BEST MODE FOR CARRYING OUT THE INVENTION

Figure 1:
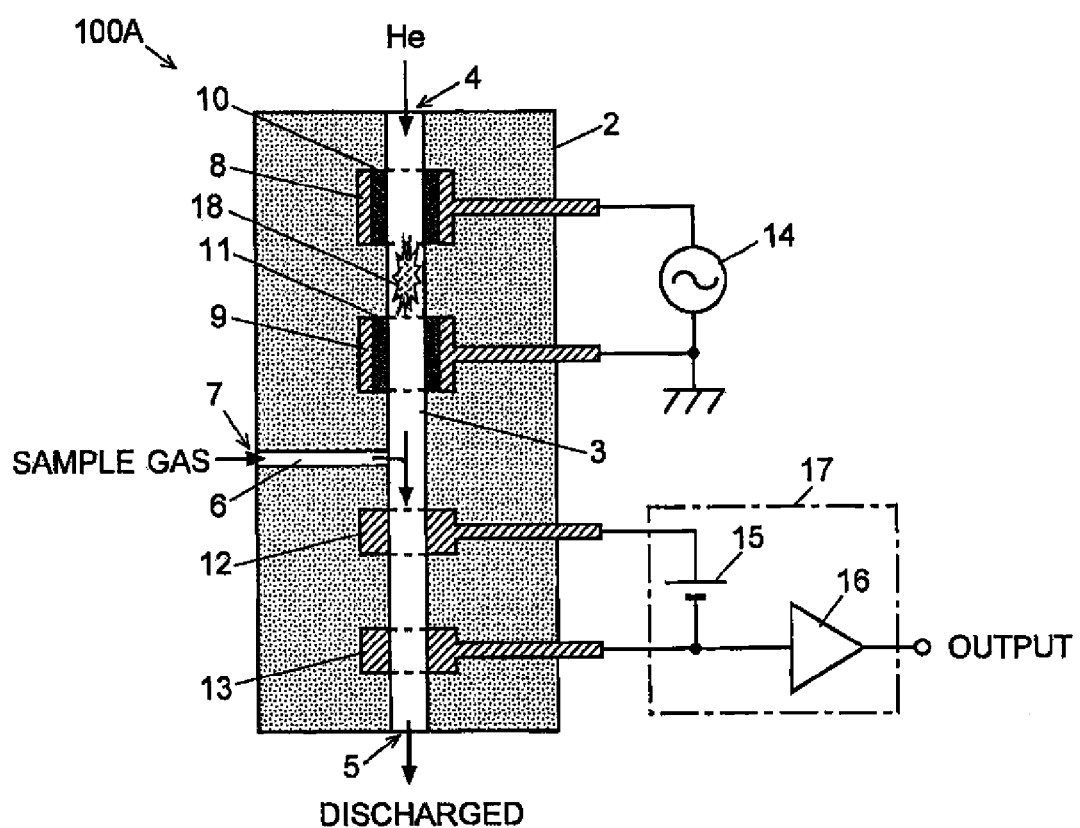
FIG. 1 is a schematic configuration diagram of a discharge ionization current detector according to a reference example of the present invention.

In advance of specific descriptions of embodiments of the discharge ionization current detector according to the present invention, a discharge ionization current detector using a low-frequency AC-excited dielectric barrier discharge is described with reference to the attached drawings. FIG. 1 is a schematic configuration diagram of one reference example of a discharge ionization current detector using a low-frequency AC-excited dielectric barrier discharge.

This discharge ionization current detector 100A has a detection cell 2 made of an insulating material, such as ceramic, an excitation high-voltage power source 14 and an ion-current detection unit 17. Inside the detection cell 2, a gas passage 3 and a sample gas introduction passage 6 are formed. The gas passage 3 has a gas supply port 4 and a gas discharge port 5 at both ends. The sample gas introduction passage 6 has a sample gas supply port 7 at its inlet end and is connected to an intermediate point of the gas passage 3. The gas passage 3 is provided with a pair of circumferential plasma generation electrodes 8 and 9 on the upstream side of the gas stream and a pair of circumferential ion-current detection electrodes 12 and 13 on the downstream side of the gas stream.

The ion-current detection electrodes 12 and 13 each have a metallic surface (or surface made of another conductive material) exposed inside the gas passage 3 so as to come in direct contact with a gas flowing through this passage. On the other hand, the plasma generation electrode 8 and 9 each consist of a metallic body (or a body made of another conductive material) on which a dielectric coating layer 10 or 11 made of ceramic, glass, polymer or other material is formed; these dielectric coating layers 10 and 11 are exposed inside the gas passage 3 so as to come in direct contact with the gas flowing through the gas passage 3. In other words, the metallic portion of the electrodes 8 and 9 are not exposed inside the gas passage 3.

Each of the electrodes 8, 9, 12 and 13 has a lead wire connected thereto outside the detection cell 2. The plasma generation electrode 8 is connected to an excitation high-voltage power source 14, while the other plasma generation electrode 9 is connected to the ground. The ion-current detection electrode 13 is connected to a current amplifier 16 for collecting electric charges, which is included in an ion-current detection unit 17, while the other ion-current detection electrode 12 is connected to a bias DC power source 15. The excitation high-voltage power source 14 generates a low-frequency high AC voltage; its frequency is within a range from 1 [kHz] to 100 [kHz], more preferably from 5 [kHz] to 50 [kHz]. The voltage amplitude is preferably within a range from 1 [kVp-p] to approximately 10 [kVp-p]. The AC voltage may have any waveform, such as sine waves, rectangular waves, triangular waves or saw-tooth waves. The method and form of the ion-current detection are not limited to the aforementioned one. For example, the ion-current detection electrodes 12 and 13 may consist of a metal wire or metal plate arranged across the gas passage 3.

The detecting operation of this discharge ionization current detector 100A is hereinafter described. As shown by the downward arrows in FIG. 1, helium, as a plasma gas, is supplied to the gas supply port 4 at a predetermined flow rate. Meanwhile, as indicated by the rightward arrow in FIG. 1, a sample gas containing a component to be analyzed is supplied into the sample gas supply port 7. The plasma gas may be any gas that can be easily ionized. Examples include argon, nitrogen, neon and xenon in addition to helium; a mixture of two or more of these gases can also be used. The helium gas and the sample gas merge with each other inside the gas passage 3 and flow downward, to be eventually discharged from the gas discharge port 5.

When the helium gas is flowing through the gas passage 3 in the previously described manner, a control signal is sent from a control circuit (not shown) to drive the excitation high-voltage power source 14, whereupon the excitation high-voltage power source 14 applies a low-frequency high AC voltage between the plasma generation electrodes 8 and 9. As a result, an electric discharge 18 occurs between the plasma generation electrodes 8 and 9. The electric discharge 18 takes place through the dielectric coating layers 10 and 11, which are respectively formed on the two electrodes 8 and 9. This means that the electric discharge 18 is a dielectric barrier discharge. By this dielectric barrier discharge, the helium gas flowing through the gas passage 3 is ionized to form plasma. This plasma is an atmospheric pressure non-equilibrium micro-plasma.

Since the metallic surfaces of the plasma generation electrodes 8 and 9 are not exposed inside the gas passage 3, no secondary electron emission occurs from these metallic surfaces and the plasma can maintain a stable state. Furthermore, in the case of the atmospheric pressure non-equilibrium plasma, the power supply from the applied voltage is temporarily cut before a sudden heating of the plasma initiates, so that the plasma hardly reaches high temperatures. The low-frequency power supply also contributes to maintaining the plasma at low temperatures. Thus, the temperature increases in the electrodes 8, 9, 12 and 13 as well as in the inner wall surface of the pipe facing the gas passage 3 are prevented. As a result, the emission of thermions from the electrodes 8, 9, 12 and 13, as well as the emission of impurity gas from the inner wall surface of the pipes or other components, are almost completely eliminated, so that a stable plasma can be formed.

The excitation light and helium-excited species emitted from the atmospheric pressure non-equilibrium micro-plasma created in the aforementioned manner reaches through the gas passage 3 to the region where the sample gas is present and ionizes the molecules (or atoms) of the sample components in the sample gas. The thereby produced sample ions impart or receive electrons to or from the ion-current detection electrode 13 due to the effect of the bias DC voltage applied to the other ion-current detection electrode 12. Thus, an ion current corresponding to the amount of the produced sample ions, i.e. the amount of sample components, is fed to the current amplifier 16, which amplifies the ion current and outputs it as a detection signal. In this manner, the present discharge ionization current detector 100A produces a detection signal corresponding to the amount (concentration) of sample component contained in an introduced sample gas. The ionization of the sample-component molecules occurs due to the action of the excitation light and helium-excited species created by the plasma. Since this plasma is maintained in a stable state due to the previously described reasons, the ionization proceeds in a stable form, producing a stable ion current.

Increasing the frequency of the excitation voltage applied to the plasma electrodes 8 and 9 increases the power supplied into the plasma and improves the ionization performance. However, setting the frequency of this excitation voltage too high will considerably increase the plasma temperature and cancel the advantages of the low-temperature plasma. Taking the trade-off between these two effects into account, it is reasonable to set the frequency of the excitation high-voltage power source 14 within a range from 5 [kHz] to 50 [kHz]. With this setting, the advantages of the use of the dielectric barrier discharge will be satisfactorily obtained.

In the previous example, a double-side dielectric barrier discharge structure is adopted; both of the plasma generation electrodes 8 and 9 respectively have the dielectric coating layer 10 and 11. The double-side dielectric barrier discharge structure is featured by the high stability of both the electric discharge itself and the plasma. However, it is also possible to remove the dielectric coating layer 11 from the grounded electrode 9 to create a single-side dielectric barrier discharge structure. The single-side dielectric barrier discharge supplies a larger amount of electrons to the plasma than the double-side dielectric barrier discharge, causing an increase in the plasma energy. As a result, the emission of the excitation light and helium-excited species increases, whereby the ionization performance can be improved. Therefore, the detection sensitivity can be improved even for a gas that is difficult to be ionized. In particular, forming the metallic surface on the plasma generation electrode 9 located in the downstream portion of the gas stream (i.e. the electrode closer to the ion-current detection unit) prevents the charged particles in the plasma from directly impinging on the ion-current detection electrodes 12 and 13. This configuration is expected to have the effect of reducing the noise and improving the S/N ratio.

Figure 2:
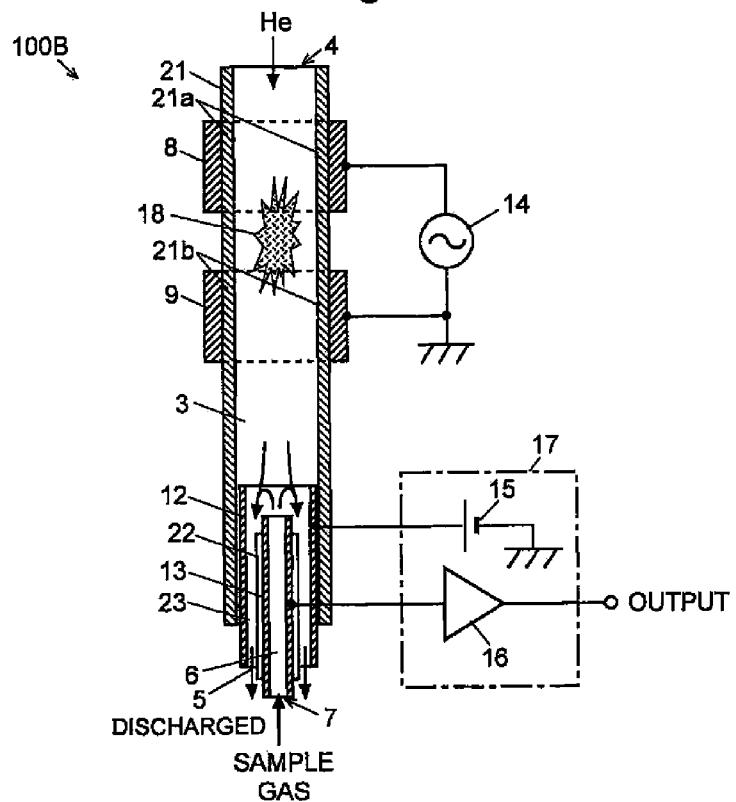
FIG. 2 is a schematic configuration diagram of a discharge ionization current detector according to another reference example of the present invention.

FIG. 2 is a schematic configuration diagram of another reference example of the discharge ionization current detector using a low-frequency AC-excited dielectric barrier discharge. The components identical or equivalent to the components described in the previous reference example are denoted by the same numerals so as to clearly show the correspondence of the components.

The present discharge ionization current detector 100B includes a cylindrical pipe 21 made of a dielectric material, such as quartz, with its inner space serving as the gas passage 3. In one example, the cylindrical pipe 21 has an outer diameter of 3.9 [mm] and inner diameter of 2.5 [mm]. On the outer wall surface of this cylindrical pipe 21, metallic plasma generation electrodes 8 and 9 are provided at a predetermined distance from each other. The plasma generation electrodes 8 and 9 are isolated from the gas passage 3 by the wall of the cylindrical pipe 21. The portions 21a and 21b of this wall, made of a dielectric material, function as the dielectric coating layer 10 and 11 of the previous reference example. Similar to the previous reference example, an excitation high-voltage power source 14 is connected between the plasma generation electrodes 8 and 9. The plasma generation electrode 8 and 9 can be easily formed, for example, by winding an electrically conductive tape made of a copper foil or similar material on the cylindrical pipe 21.

The ion-current detection electrodes 12 and 13 are a coaxial double-pipe structure between which an insulation pipe 22 made of aluminum oxide or similar substance is located. The outer one of the double pipes is the ion-current detection electrode 12 to which a bias AC voltage is applied, while the inner pipe serves as the ion-current detection electrode 13 for collecting electric charges. The inner and outer pipes are made of, for example, platinum. In one example, the outer diameters of the inner pipe, outer pipe and insulation pipe 22 are 0.7 [mm], 2.0 [mm] and 1.2 [mm], respectively.

The inside of the inner pipe serving as the ion-current detection electrode 13 corresponds to the sample-gas introduction passage 6. As shown by the upward arrow in FIG. 2, a sample gas is supplied from the sample-gas supply port 7 at the lower end of the inner pipe into the sample-gas introduction passage 6. The helium gas, which is supplied to the gas supply port 4 at the upper end of the cylindrical pipe 21, flows downwards through the gas passage 3 to be merged with the sample gas flowing upwards through the sample-gas introduction passage 6. The merged gas flows downwards through a merging passage 23 formed between the outer pipe and the insulation pipe 22 located on the outside of the inner pipe, to be eventually discharged from the gas discharge port 5 at the lower end of the outer pipe serving as the ion-current detection electrode 12.

The operation of detecting a sample component contained in the sample gas is the same as the previous reference example. That is, with helium flowing through the gas passage 3, an AC voltage of approximately 1 [kVp-p]-10 [kVp-p] and 1 [kHz]-100 [kHz] is applied between the plasma generation electrodes 8 and 9. As a result, an electric discharge, which is a dielectric barrier discharge, occurs within the gas passage 3 via the dielectric material of the portions 21*a* and 21*b* of the wall, whereby an atmospheric pressure non-equilibrium micro-plasma is generated. Due to the action of the excitation light emitted from this plasma and the helium-excited species generated within the plasma, the sample-component molecules in the sample gas are ionized. Due to the generated sample ions, an ion current flows through the ion-current detection electrode 13, and a detection signal is outputted from the ion-current detection unit 17. Similar to the previous reference example, since the atmospheric pressure non-equilibrium plasma is generated in a stable form, the ionization of the sample components proceeds in a stable manner, so that a stable detection signal can be extracted.

Figure 3:
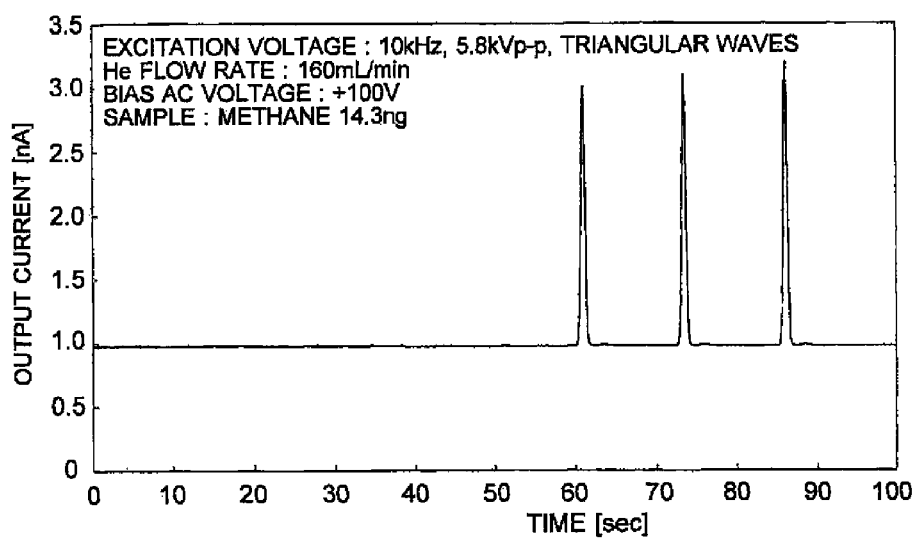
FIG. 3 is a graph showing a measurement example using the discharge ionization current detector according to the reference example of FIG. 2.

FIG. 3 is a graph showing a measurement example using the discharge ionization current detector 100B having the configuration shown in FIG. 2. The measurement conditions were as follows: The excitation voltage was in the form of bipolar triangular waves with a frequency of 10[kHz] and amplitude of 5.8[kVp-p]; the bias DC voltage was +100[V]; and the flow rate of helium gas was 160 [ml/min]. The sample gas was 14.3 [ng] of methane ($CH_4$). The graph of FIG. 3 shows the detection signals obtained when this sample gas was supplied three times, like a series of pulses, at intervals of 10 [s]. It demonstrates that an adequately high peak of the output current was obtained.

Figure 4:
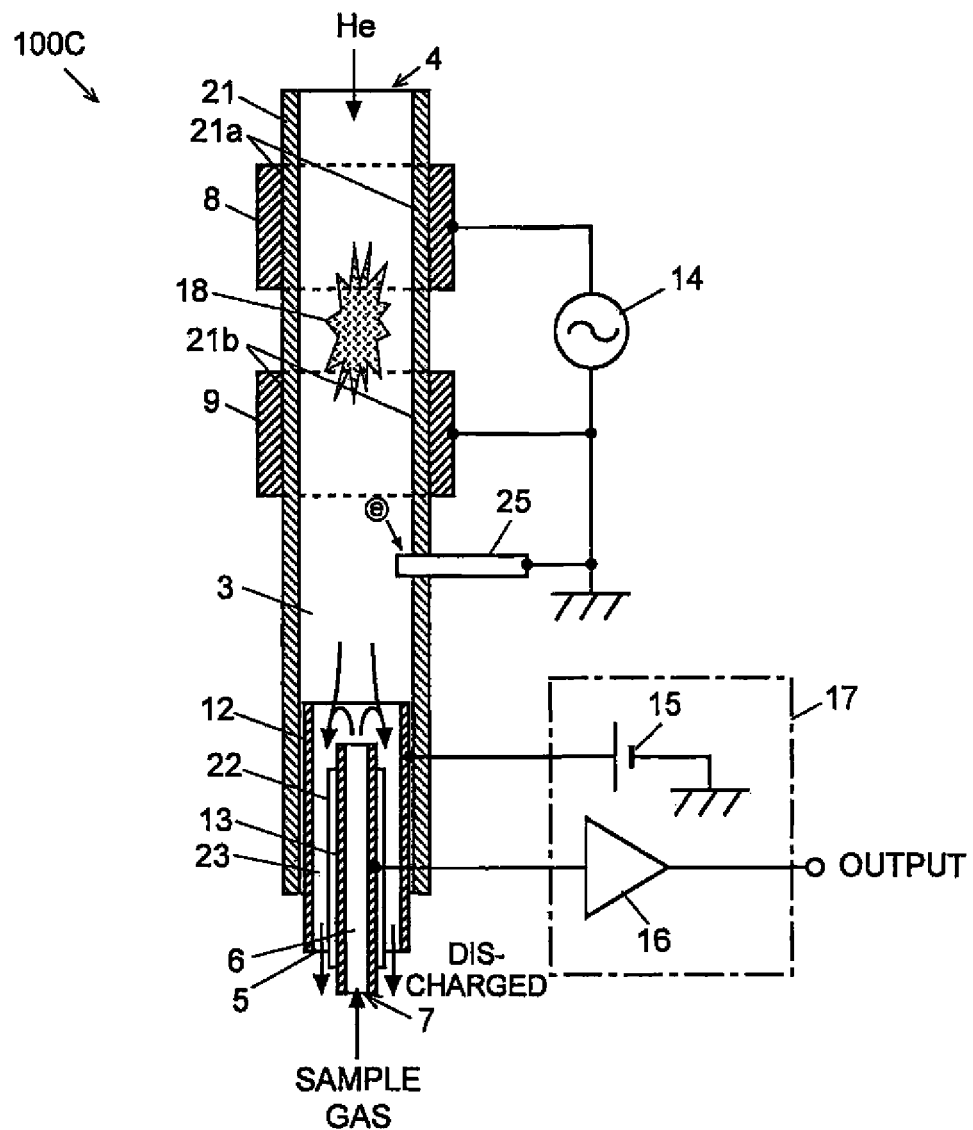
FIG. 4 is a schematic configuration diagram of a discharge ionization current detector according to another reference example of the present invention.

FIG. 4 is a schematic configuration diagram of a discharge ionization current detector, which is a modified example of the configuration shown in FIG. 2. The basic configuration is the same as shown in FIG. 2. In addition, an electrically conductive electrode 25, which is made of platinum, copper wire or similar element, is provided in the gas passage 3 between the plasma generation electrode 9 and the ion-current detection electrodes 12 and 13. This electrode 25 is grounded. Similar to the previous case of providing a metallic surface in the plasma generation electrode 9 on the downstream side of the gas flow, the provision of the electrically conductive electrode 25 has the effect of preventing the electric charges generated in the plasma from directly impinging on the ion-current detection electrodes 12 and 13, whereby noises are reduced and the S/N ratio is improved.

As compared to the pulsed discharge ionization current detector, the previously described discharge ionization current detector using a low-frequency AC-Excited dielectric barrier discharge can generate plasma in a more stable manner and thereby improve the S/N ratio of the detection signal. However, when the concentration of the sample gas is high, the light emitted from the plasma attenuates in the sample gas, causing a decrease in the ionization efficiency. Furthermore, since the ions generated from the sample gas have a rather short life, if the distance between the ion generation area and the ion-current detection electrodes is large, a high percentage of ions will become extinct before they reach the ion-current detection electrodes, which decreases the ion collection efficiency. Due to these reasons, it is impossible to increase the dynamic range. The following descriptions focus on embodiments of the discharge ionization current detector according to the first aspect of the present invention which includes improvements in the aforementioned points.

[First Embodiment]

Figure 5:
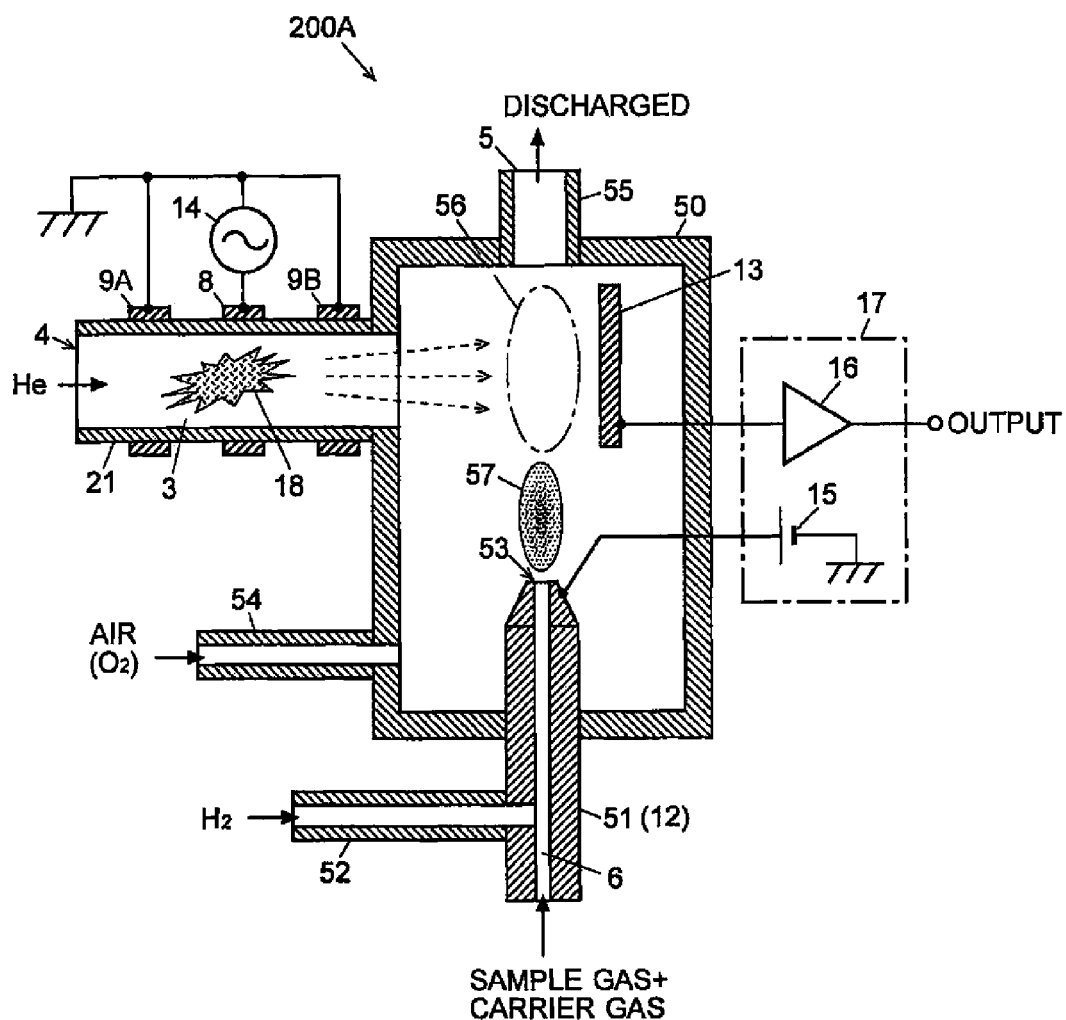
FIG. 5 is a schematic configuration diagram of a discharge ionization current detector according to the first embodiment of the present invention.

A discharge ionization current detector according to the first embodiment of the first aspect of the present invention is hereinafter described. FIG. 5 is a schematic configuration diagram of the discharge ionization current detector 200A according to the first embodiment. The same numerals are assigned to the components identical or equivalent to those already described in the previous reference examples.

The discharge ionization current detector 200A of the present embodiment has a substantially hermetically sealed detection cell 50 having a hydrogen flame formation nozzle 51. A cylindrical pipe 21, combustion air supply pipe 54 and discharge pipe 55 are connected to the detection cell 50. The cylindrical pipe 21 is made of a dielectric material, such as quartz, with a gas passage 3 formed inside. A hydrogen supply pipe 52 is connected to the hydrogen flame formation nozzle 51; the portion of the passage lower than the connection point corresponds to the sample-gas introduction passage 6. Inside the detection cell 50, an ion-current collection electrode 13, which is one of the paired ion-current detection electrodes, is provided above the hydrogen flame formation nozzle 51. The hydrogen flame formation nozzle 51, which is a conductor connected to a bias DC power source 15, functions as the bias-voltage application electrode 12, i.e. the other of the paired ion-current detection electrodes. Three plasma generation electrodes 8, 9A and 9B are arranged along the gas passage 3; the central plasma generation electrode 8 is connected to an excitation voltage power source 14, while the other two plasma generation electrodes 9A and 9B located on both sides of the central electrode 8 are connected to the ground.

The detecting operation of this discharge ionization current detector 200A is hereinafter described. As shown by an upward arrow in FIG. 5, a carrier gas containing a sample gas is supplied into the sample-gas introduction passage 6. Subsequently, this carrier gas is mixed with hydrogen gas supplied into the hydrogen supply pipe 52. The mixed gas spouts from the exit port 53 of the hydrogen flame formation nozzle 51 into the detection cell 50. Then, the mixed gas burns due to the action of the air (or oxygen) supplied through the combustion air supply pipe 54, forming a hydrogen flame 57. Meanwhile, helium, as a plasma gas, is supplied to the gas supply port 4 at a predetermined flow rate. As already noted, the plasma gas may be any gas that can be easily ionized. Examples include argon, nitrogen, neon and xenon in addition to helium; a mixture of two or more of these gases can also be used.

When the helium gas is flowing through the gas passage 3, a control signal is sent from a control circuit (not shown) to drive the excitation high-voltage power source 14, whereupon the excitation high-voltage power source 14 applies a high AC voltage (approximately 1-20 [kVp-p]) having a low-frequency (1-100 [khz], and more preferably 5-50 [kHz]) between the plasma generation electrodes 8 and 9. As a result, an electric discharge 18, which is a dielectric barrier discharge, occurs between the plasma generation electrodes 8, 9A and 9B, whereby the helium gas flowing through the gas passage 3 is ionized, generating a plasma. The structure in which the electrode 8 to which the high voltage is applied is sandwiched between the grounded electrodes 9A and 9B prevents the plasma produced by the electric discharge from spreading toward the upstream and downstream sides of the gas flow, thereby limiting the substantial plasma generation to the space between the two plasma generation electrodes 9A and 9B. (Refer to Kitano et al., "Atmospheric-pressure LF microplasma jet", *Oyo Buturi*, Vol. 77, No. 4 (2008), pp. 383-389.)

The light emitted from the plasma generated in the gas passage 3 (and from the discharge 18 itself) is introduced into the detection cell 50 and thrown onto the flow of the mixed gas spouting from the exit port 53 in the vicinity of the ionization area 56 located before the ion-current collection electrode 13. A portion of the sample components in the sample gas spouting from the exit port 53 is ionized in the hydrogen flame 57, while most of those components remain in the unionized form until they reach the ionization area 56, where the sample-component molecules are ionized due to the action of the excitation light emitted from the plasma. Water molecules are formed in the hydrogen flame 57 due to the combustion process. These molecules can combine with the sample-molecule ions generated in the vicinity of the ionization area 56, forming hydrated ions, or react with the sample-molecule ion to form hydroxonium ions, which is a kind of hydrated ion.

As already explained, hydrated ions (such as the hydroxonium ion) live longer than non-hydrated ions. Furthermore, the ionization area 56 is closer to the ion-current collection electrode 13. The hydrated ions of the sample-molecule ions and hydroxonium ions efficiently reach the ion-current collection electrode 13 (without becoming extinct halfway) by being attracted due to the effect of the DC electric field created by a DC bias voltage of approximately 50-300[V] applied between the hydrogen flame formation nozzle 51 (bias-voltage application electrode 12) and the ion-current collection electrode 13. Then, the sample-molecule ions and hydroxonium ions impart or receive electrons to or from the ion-current collection electrode 13. Thus, an ion current corresponding to the amount of the produced sample ions, i.e. the amount of sample components, is fed to the current amplifier 16, which amplifies the ion current and outputs it as a detection signal. In this manner, the present discharge ionization current detector 200A produces a detection signal corresponding to the amount (concentration) of sample components contained in an introduced sample gas.

Due to not only the increase in the percentage of the sample-molecule ions that reach the ion-current collection electrode 13 after being generated from the plasma by the action of the excitation light or the like, but also the improvement in the ionization efficiency due to the generation of sample-molecule ions by combustion of the sample gas in the hydrogen flame 57, the ion-current collection electrode 13 receives a larger amount of sample-molecule ions than in the conventional discharge ionization current detectors. Therefore, even a low-concentration sample that cannot be detected by conventional methods can be detected. Thus, the dynamic range is improved.

[Second Embodiment]

Figure 6:
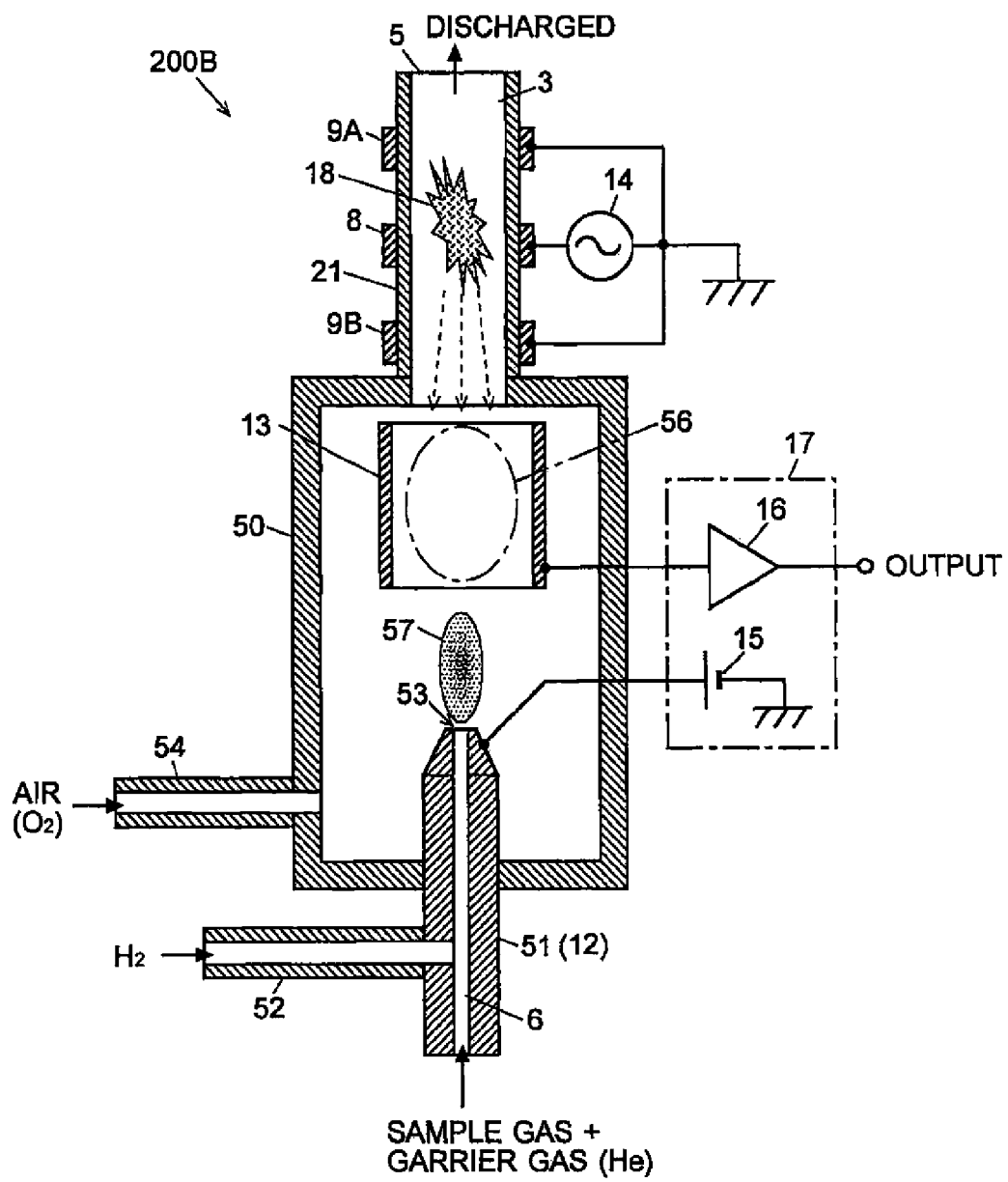
FIG. 6 is a schematic configuration diagram of a discharge ionization current detector according to the second embodiment of the present invention.

A discharge ionization current detector according to the second embodiment of the present invention is hereinafter described. FIG. 6 is a schematic configuration diagram of the discharge ionization current detector 200B according to the second embodiment. The same numerals are assigned to the components identical or equivalent to those already described in the first embodiment and the previous reference examples.

In the second embodiment, the cylindrical pipe 21 with circumferentially provided plasma generation electrodes 8, 9A and 9B serves as the exhaust pipe and is connected to the ceiling of the detection cell 50 so that it opposes the exit port 53 of the hydrogen flame formation nozzle 51. The ion-current collection electrode 13, which is placed between the hydrogen flame formation nozzle 51 and the cylindrical pipe 21, has a cylindrical shape. This is to increase the area of the electrode.

In the discharge ionization current detector 200B of the second embodiment, no helium gas is supplied as the plasma gas into the gas passage 3; instead, another helium gas, which is supplied into the sample-gas introduction passage 6 as a carrier gas with a sample gas, is used as the plasma gas. The carrier gas is spouted from the hydrogen flame formation nozzle 51 into the detection cell 50 and then transferred from the detection cell 50 to the upper end of the gas passage 3, to be eventually discharged from the gas discharge port 5. In this process, helium is ionized by the electric discharge 18, generating an atmospheric pressure non-equilibrium microplasma. This plasma emits excitation light, which ionizes the sample molecules passing through the hydrogen flame 57. Furthermore, hydrated ions of the sample-molecule ions as well as hydroxonium ions are generated due to the action of the water molecules generated by the hydrogen flame 57. The mechanism for detecting these ions is the same as in the first embodiment.

The overall structure of the second embodiment is simpler than that of the first embodiment. The piping for supplying the gases to the detection cell 50 is also simplified. However, the inner wall of the cylindrical pipe 21 becomes easily stained since the exhaust gas resulting from the burning of the hydrogen flame 57 passes through the gas passage 3. Therefore, it is necessary to clean it more frequently.

[Third Embodiment]

Figure 7:
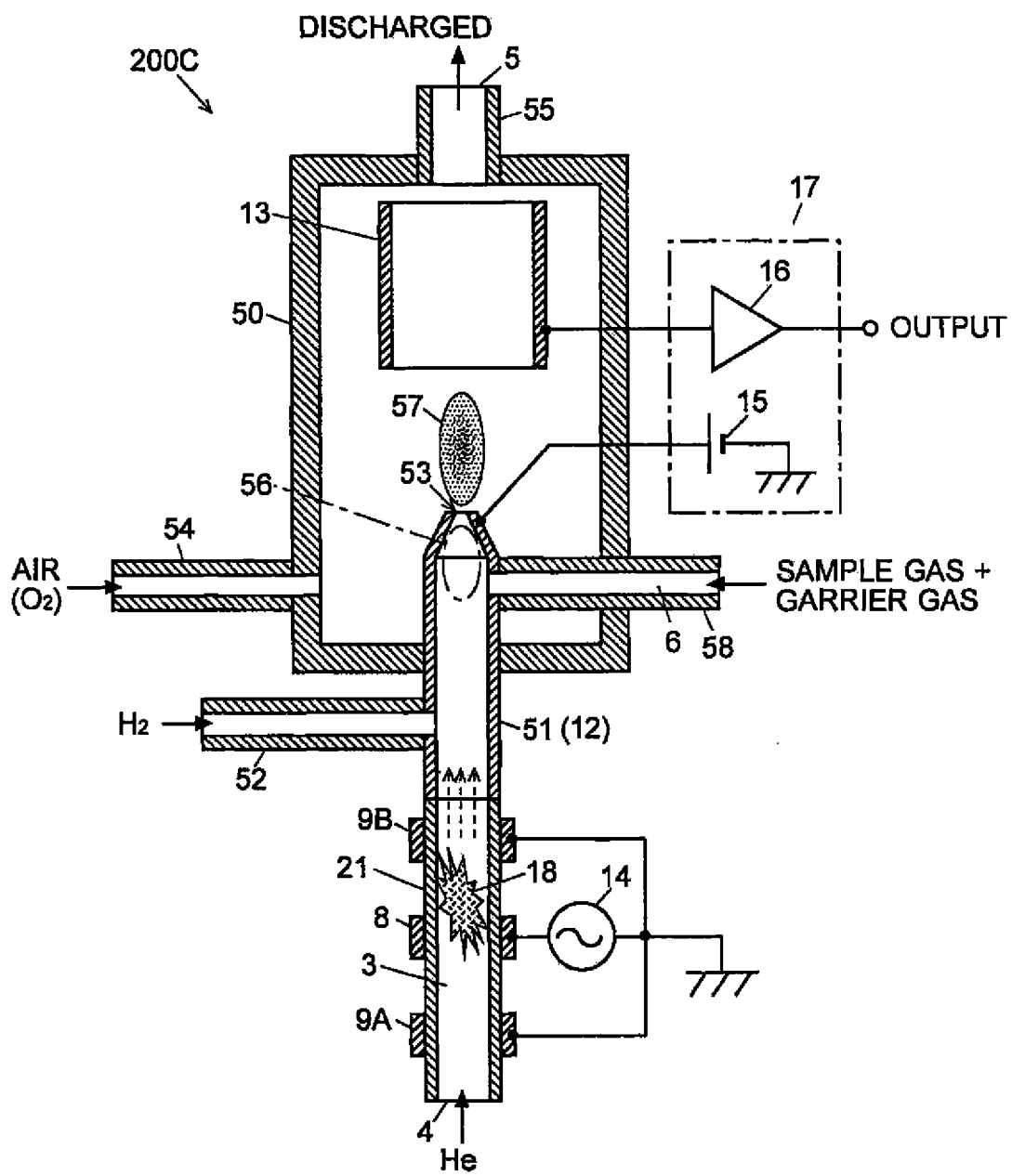
FIG. 7 is a schematic configuration diagram of a discharge ionization current detector according to the third embodiment of the present invention.

A discharge ionization current detector according to the third embodiment of the present invention is hereinafter described. FIG. 7 is a schematic configuration diagram of the discharge ionization current detector 200C according to the third embodiment. The same numerals are assigned to the components identical or equivalent to those already described in the first and second embodiments as well as the previous reference examples.

In the third embodiment, the cylindrical pipe 21 having the plasma generation electrode 8, 9A and 9B is not connected to the detection cell 50 but the inlet end of the hydrogen flame formation nozzle 51. A sample-gas introduction pipe 58 with the sample-gas introduction passage 6 formed inside is connected to a point near the tip of the hydrogen flame formation nozzle 51. The internal passage of the hydrogen flame formation nozzle 51 is widened so that the light emitted from the plasma can easily pass through it.

In the discharge ionization current detector 200C of the third embodiment, helium gas as the plasma gas is supplied into the gas passage 3 as shown by the upward arrows in FIG. 7, and plasma is generated by the discharge 18. Hydrogen gas supplied through the hydrogen supply pipe 52 and a sample gas supplied through the sample gas introduction pipe 58 are mixed together within the passage of the hydrogen flame formation nozzle 51, where an excitation light from the plasma is introduced. Thus, this passage also functions as the ionization area 56. Therefore, the sample molecules in the sample gas are ionized in the ionization area 56 of the hydrogen flame formation nozzle 51, and those sample-molecule ions immediately pass through the hydrogen flame 57 immediately after they spout from the exit port 53. When passing through the hydrogen flame 57, the ions combine with water molecules produced in the hydrogen flame 58, forming hydrated ions or hydroxonium ion. Then, the thereby formed hydrated ions and hydroxonium ion reach the ion-current collection electrode 13, to be detected by an ion-detection mechanism, which is the same as used in the first embodiment.

[Fourth Embodiment]

Figure 8:
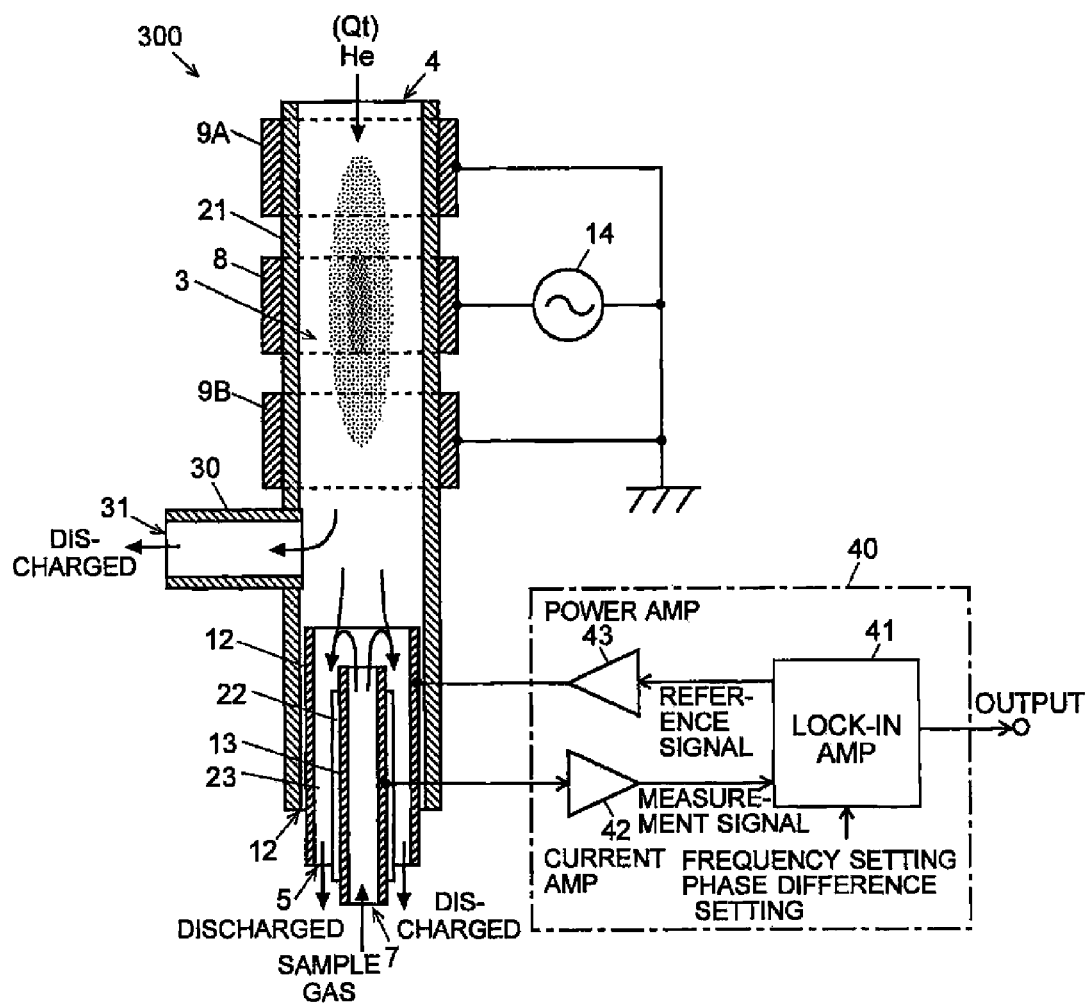
FIG. 8 is a schematic configuration diagram of a discharge ionization current detector according to the fourth embodiment of the present invention.

A discharge ionization current detector according to one embodiment (the fourth embodiment) of the second aspect of the present invention is hereinafter described. FIG. 8 is a schematic configuration diagram of the discharge ionization current detector according to the fourth embodiment. The same numerals are assigned to the components identical or equivalent to those already described in the first through third embodiments as well as the previous reference examples. It should be noted that the present discharge ionization current detector 300 does not use any hydrogen flame as in the first through third embodiments; it is primarily featured by an improved detection system for reducing noises to widen its dynamic range.

The basic structure of the discharge ionization current detector 300 according to the fourth embodiment is similar to the structure of the reference example shown in FIG. 2. One major difference exists in that, similar to the first through third embodiments, three plasma generation electrodes 8, 9A and 9B are arranged along the gas passage 3; the central plasma generation electrode 8 is connected to an excitation voltage power source 14 while the other two plasma generation electrodes 9A and 9B located on both sides of the central electrode 8 are connected to the ground. As already explained, the structure in which the electrode having a high voltage applied thereto is sandwiched between the grounded electrodes 9A and 9B prevents the plasma produced by the electric discharge from spreading toward the upstream and downstream sides of the gas flow, thereby limiting the substantial plasma generation to the space between the two plasma generation electrodes 9A and 9B.

Furthermore, a branch exhaust pipe 30 is connected to the gas passage 3 at a point between the aforementioned plasma generation area and an ion-current detection area, in which the downward flow of the helium gas and the upward flow of the sample gas merge together and the sample components in the sample gas are ionized and detected. A portion of the helium gas flowing from the upstream side is introduced into the branch exhaust pipe 30, to be eventually discharged from the discharge port 31. The branching ratio is determined by the flow-resistance ratio of the passages on the downstream side of the branching point. In the present embodiment, the diameters, lengths and other dimensions of the pipes are chosen so that the flow resistances of the passages are approximately equalized. Accordingly, approximately one half of the helium gas introduced from the gas supply port 4 into the gas passage 3 flows into the branch exhaust pipe 30 and the remaining one half into the ion-current detection area.

The supplied helium contains a slight but non-negligible amount of impurities. Furthermore, impurities may also be emitted from the inner wall surface of the cylindrical pipe 21. These impurities are small in quantity yet easy to be directly excited by plasma and turn into ions. When these ions reach the ion-current detection electrodes 12 and 13, they create a noise, which destabilizes the detection output. To cope with this problem, a portion of helium gas that has passed through the plasma generation area is discharged before it reaches the ion-current detection area. This operation is intended to discharge a portion of the impurities and decrease the amount of impurities reaching the ion-current detection area. Thus, the aforementioned noise can be reduced. In this process, a portion of the helium-excited species generated in the plasma is also discharged with the helium gas. However, in the case of the low-frequency AC-excited dielectric barrier discharge, it is the excitation light from the plasma that most dominantly affects the ionization of the sample components. Therefore, the ionization efficiency will be maintained at substantially the same level if an adequate amount of excitation light is supplied to the ion-current detection area.

As already noted, the most important feature of the discharge ionization current detector 300 of the fourth embodiment exists in its ion-current detection method. More specifically, a lock-in detection method is adopted in the fourth embodiment, and the ion-current detection unit 40 includes a lock-in amplifier 41, current amplifier 42, and power amplifier 43. The ion-current detection electrode 13 is connected to the input of the current amplifier 42, while the other ion-current detection electrode 12 is connected to the output of the power amplifier 43. Though not shown in the figure, the lock-in amplifier 41 includes a reference signal generator for generating a reference signal, a phase shifter for adjusting the phase of the reference signal, a phase-sensitive detector for performing a phase-locked detection of measurement signals with respect to the reference signal by a switching operation, and a low-pass filter for removing high-frequency components with respect to the synchronously detected signal.

The operation of ionizing the sample components in a sample gas is basically the same as in the reference sample and hence will not be described; the following description focuses on the ion-current detection operation. The lock-in amplifier 41 produces a reference signal of a predetermined frequency. The power amplifier 43 amplifies the power of this signal and applies it to the ion-current detection electrode 12 as the AC bias voltage. This voltage creates an AC electric field in the ion-current detection area. Due to this electric field, ions originating from the sample components oscillate and reach the ion-current detection electrode 13. The ionization current signal obtained at this ion-current detection electrode 13 is converted from current to voltage and then fed to the lock-in amplifier 41 as a measurement signal. From this measurement signal, the lock-in amplifier 41 extracts a signal having the same frequency component as that of the reference signal. An ion originating from the sample component of interest has the same frequency component as that of the reference signal, whereas the frequencies of disturbing noises attributable to the measurement system (e.g. an electromagnetic noise flying into a signal cable, a noise resulting from a thermo-electromotive force due to a temperature fluctuation, and so on) differ from that of the reference signal. Therefore, it is possible to effectively remove such disturbing noises to obtain a detection output with a high level of S/N ratio.

For the lock-in detection, it is necessary to previously set the frequency of the reference signal (i.e. the lock-in frequency) and the phase difference between the reference signal and the measurement signal). The lock-in detection is accompanied by superposition of unwanted current components due to the parasite capacitance of each element of the ion-current detection electrodes 12 and 13, the ion-current detection unit 40, as well as the signal cables connecting them.

Figure 9:
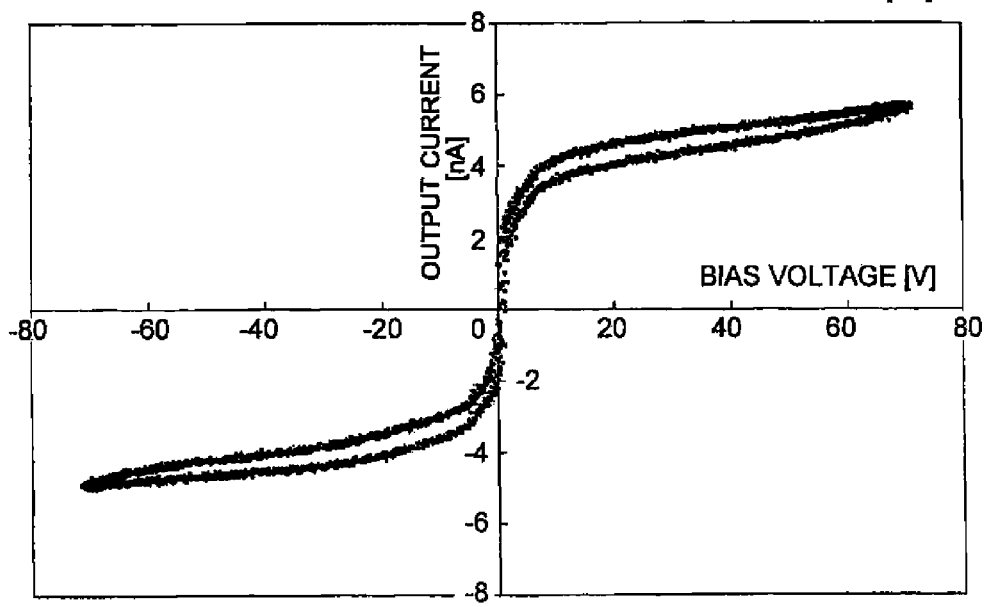
FIG. 9 is a graph showing an example of a voltage-current curve actually measured for an AC bias voltage having a frequency of 0.01 [Hz].
Figure 10:
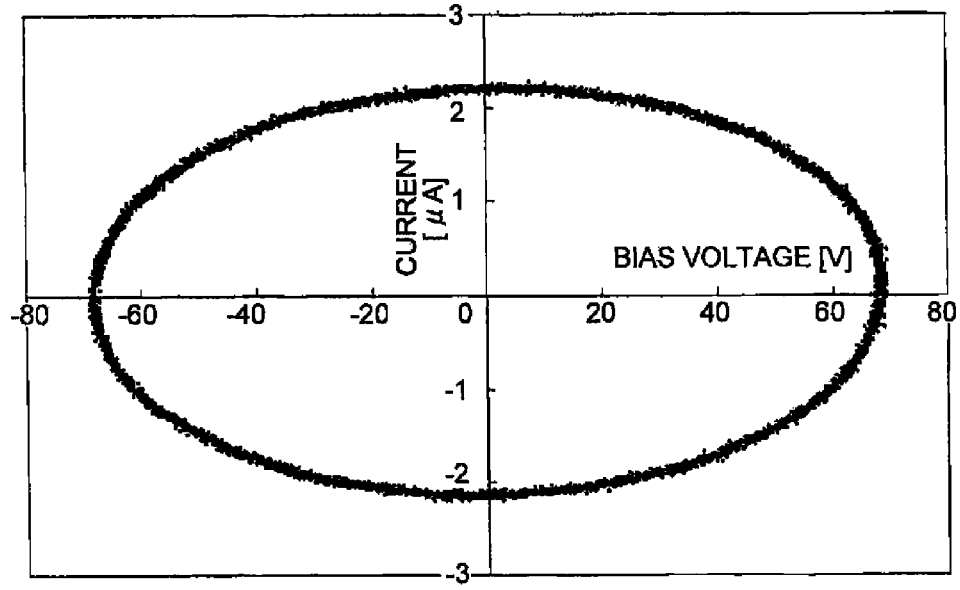
FIG. 10 is a graph showing an example of a voltage-current curve actually measured for an AC bias voltage having a frequency of 1 [kHz].

FIG. 9 is the result of a measurement of a current signal obtained by varying the amplitude of the AC bias voltage with the frequency of the AC bias voltage (i.e. the reference signal) set at 0.01 [Hz]. This result demonstrates that, in the present case, the ionization current (a few to several nA) can be almost directly measured since the frequency is so low that the current of the capacitance component barely flows. On the other hand, when the frequency of the AC bias voltage was set at 1 [kHz], the measured result of the current signal with respect to the amplitude of the AC bias voltage was as shown in FIG. 10. (It should be noted that the vertical scale in this figure is different from the one in FIG. 9.) This result shows that a current of the capacitance component as high as the levels of micro-amperes flows in this case. However, as is evident from the shape of the voltage-current curve in FIG. 10, the current due to the capacitance component has a phase difference of approximately 90 degrees from the bias voltage. On the other hand, the phase difference of the signal component due to the ion current originating from the sample components is approximately zero. Therefore, it is possible to extract only the ion-current signal originating from the sample components and exclude the current component due to the parasite capacitance by previously setting the phase difference so that the current signal (i.e. the output of the lock-in amplifier 41) will become zero when no plasma is generated.

In most cases, the aforementioned parasite capacitance is determined by the configuration and structure of the apparatus. In such cases, for example, the manufacturer of the present discharge ionization current detector can perform the setting of the phase difference during the adjustment process before the shipping. When the parasite capacitance depends on not only the configuration and structure of the apparatus but also some other factors, such as the ambient temperature, the apparatus may automatically set the phase difference so that the output of the lock-in amplifier 41 becomes zero in the warming-up phase, where no plasma is generated.

Figure 11:
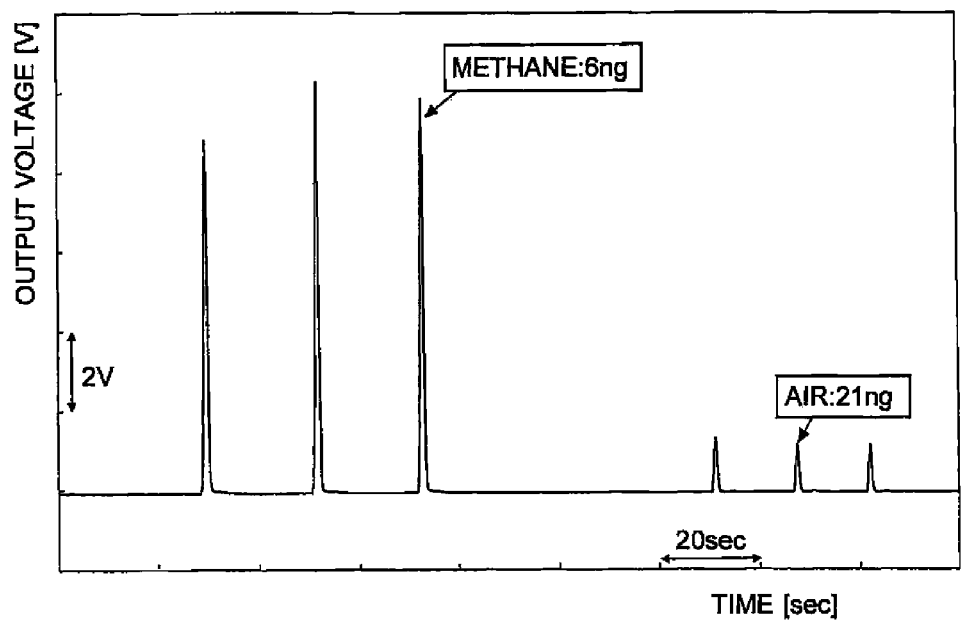
FIG. 11 is a graph showing a measurement example using the discharge ionization current detector of the fourth embodiment.

FIG. 11 is a graph showing a measurement example using the discharge ionization current detector 300 of the fourth embodiment. The parameter setting of the ion-current detection unit 40 was as follows: lock-in frequency, 1 [kHz]; amplitude of AC bias voltage, 80 [Vp-p]; and conversion gain of the current amplifier, $\times 10^5$ [V/A]. The other measurement conditions were as follows: The excitation voltage was in the form of bipolar triangular waves with a frequency of 11 [kHz] and amplitude of 5.4 [kVp-p]; and the flow rate of helium gas was 95 [mL/min]. The sample gas was methane ($CH_4$), and 6 [ng] of this gas was injected three times with a syringe, after which 21 [ng] of air was injected three times with the syringe. The graph of FIG. 11 shows the result of this analysis, which demonstrates that the obtained lock-in output signal had adequately large magnitudes; its peak-intensity variation is within the measurement error of the syringe.

Figure 12:
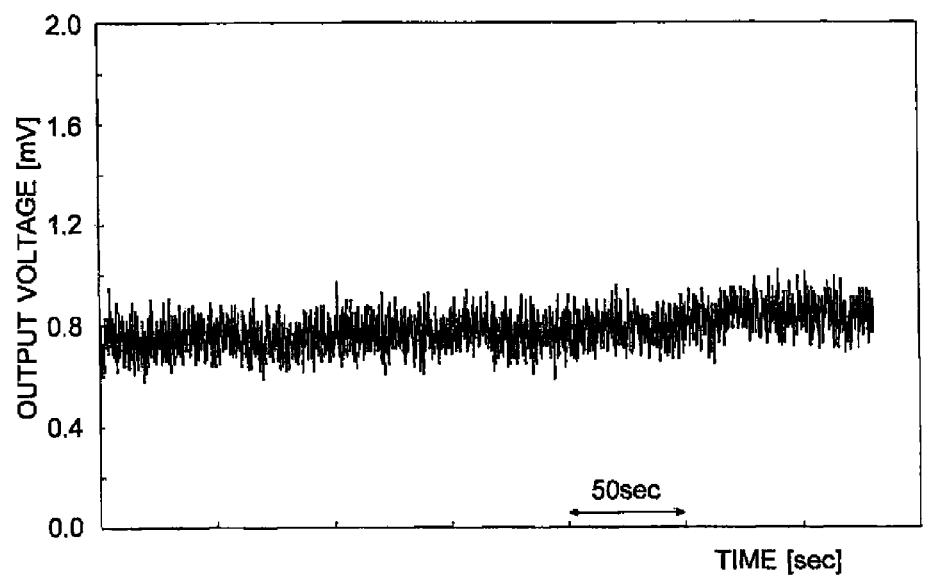
FIG. 12 is a graph showing an example of the noise measurement of a lock-in output.

FIG. 12 is the result of a measurement of the noises in the lock-in output signal. As shown, a stable output signal was obtained, with low-frequency noises under 10 [Hz] barely observed. A calculation of the detection limit on the basis of the peak signals shown in FIG. 11 and the amplitude of the noises shown FIG. 12 shows that the detection limit for methane is 0.7 [pgC/sec] (provided that the S/N ratio is 3). The S/N ratio is adequately high as compared to hydrogen flame ionization detectors, whose detection limit is not less than 3 [pgC/sec]. For comparison with this result, the ion current was measured without performing the lock-in detection under the same conditions except that the DC bias voltage was 100[V]. In this case the detection limit was within a range from 7 to 20 [pgC/sec]. Thus, it has been confirmed that a noise reduction effect can be obtained by the lock-in detection.

For example, the low-frequency disturbing noises originating from the measurement system may be an electromagnetic noise flying into a signal cable or a noise resulting from a thermo-electromotive force due to a temperature difference between the present detector and the ambient temperature. The detector needs to have one or more openings for introducing a sample gas or plasma gas and discharging a gas, and it is impossible to completely prevent intrusion of external noises through these openings. Furthermore, since the detector may be heated to a maximum temperature of approximately 400 degrees Celsius to detect a low-boiling gas, it is difficult to completely eliminate the influence of the thermo-electromotive force that occurs between the detector and its control circuit, which is at room temperature. Due to these reasons, it is normally difficult to reduce the low-frequency noises. However, by using the lock-in detection in the previously described manner, it is possible to adequately suppress the low-frequency noises and thereby lower the detection limit.

Naturally, it is possible to apply the detection method adopted in the fourth embodiment to the first through third embodiments, in which case the amount of ions reaching the ion-current collection electrode 13 increases while the noises (particularly, low-frequency noises) are reduced to be lower than ever before. This is further advantageous to the widening of the dynamic range.

It should be noted that any of the previous embodiments is a mere example of the present invention. It is evident that any change, modification or addition appropriately made within the spirit of the present invention will be included within the scope of claims of the present patent application.

The invention claimed is:

1. A discharge ionization current detector comprising:
    a discharge generation means for generating plasma from a predetermined gas by electric discharge;
    a current detection means with a detection electrode for detecting an ion current due to a gaseous sample component ionized by irradiation with light emitted from the plasma generated by the discharge generation means; and
    a flame formation means for forming a hydrogen flame by burning a mixture of hydrogen and either air or oxygen so as to supply a water molecule either into an ionization area where the ionization of a sample component due to the irradiation with light occurs or into a space between the ionization area and the detection electrode.

2. The discharge ionization current detector according to claim 1, which is characterized in that the flame formation means is placed so that the hydrogen flame is formed in an upstream portion of a sample-gas stream containing the sample component supplied into the ionization area.

3. The discharge ionization current detector according to claim 1, which is characterized in that the flame formation means is placed so that the hydrogen flame is formed between the ionization area and the detection electrode, in a sample-gas stream supplied so that the sample gas flows via the ionization area to the detection electrode.

4. The discharge ionization current detector according to claim 1, which is characterized in that the flame formation means is placed so that the hydrogen flame is formed on an upstream side of the ionization area, in a plasma-gas stream supplied so that the plasma gas flows via a plasma creation area, where the plasma is generated by electric discharge caused by the discharge generation means, to the ionization area.

5. A discharge ionization current detector comprising:
   a pair of discharge electrodes, at least one of the discharge electrodes having a surface covered with a dielectric material, for generating plasma from a predetermined as by electric discharge;
   a voltage application means for applying an AC voltage having a frequency within a range from 1 [kHz] to 100 [kHz] to the discharge electrodes;
   a current detection means with a detection electrode for detecting an ion current due to a gaseous sample component ionized by irradiation with light emitted from the plasma generated by the discharge electrodes; and
   a flame formation means for forming a hydrogen flame by burning a mixture of hydrogen and either air or oxygen so as to supply a water molecule either into an ionization area where the ionization of a sample component due to the irradiation with light occurs or into a space between the ionization area and the detection electrode.

6. The discharge ionization current detector according to claim 5, which is characterized in that the predetermined gas is selected from a group consisting of helium, argon, nitrogen, neon, xenon, and any mixture of these gases.

7. The discharge ionization current detector according to claim 5, which is characterized in that the dielectric material is silica glass.

8. The discharge ionization current detector according to claim 5, which is characterized in that the current detection means comprises:
   a pair of detection electrodes;
   a bias-voltage application means for applying an AC bias voltage having a predetermined frequency to one of the detection electrodes; and
   a lock-in detection means for performing a lock-in detection of a signal obtained from the other detection electrode with respect to a reference signal having a same frequency as that of the AC bias voltage.

9. The discharge ionization current detector according to claim 8, which is characterized in that a detection phase difference of the lock-in detection means is set so that a detection output obtained by the lock-in detection means becomes zero when no plasma is generated by the discharge generation means.

10. A discharge ionization current detector comprising:
    a detection cell having an ionization area;
    a gas passage member provided external to and attached to the detection cell, said gas passage member configured to be supplied with a predetermined gas;
    a plurality of discharge electrodes connected to the gas passage member for generating plasma within the gas passage member by electric discharge, wherein the gas passage member and the discharge electrodes are configured such that light from the plasma is emitted to the ionization area;
    a current detector with a detection electrode for detecting an ion current due to a gaseous sample component ionized by irradiation with light emitted from the plasma generated by the discharge electrodes, wherein the detection electrode is provided within the cell detector; and
    a flame formation member for forming a hydrogen flame by burning a mixture of hydrogen and either air or oxygen so as to supply a water molecule either into an ionization area where the ionization of a sample component due to the irradiation with light occurs or into a space between the ionization area and the detection electrode.

11. The discharge ionization current detector according to claim 10, wherein the predetermined gas is selected from a group consisting of helium, argon, nitrogen, neon, xenon, and any mixture of these gases.

12. The discharge ionization current detector according to claim 10, wherein the discharge electrodes are covered with a dielectric material, which is silica glass.

13. The discharge ionization current detector according to claim 10, wherein the current detector comprises:
    a pair of detection electrodes;
    a bias-voltage application unit for applying an AC bias voltage having a predetermined frequency to one of the detection electrodes; and
    a lock-in detection unit for performing a lock-in detection of a signal obtained from the other detection electrode with respect to a reference signal having a same frequency as that of the AC bias voltage.

14. The discharge ionization current detector according to claim 13, wherein a detection phase difference of the lock-in detection unit is set so that a detection output obtained by the lock-in detection unit becomes zero when no plasma is generated by the discharge electrodes.

15. The discharge ionization current detector according to claim 10, further comprising:
    a voltage application unit for applying an AC voltage having a frequency within a range from 1 [kHz] to 100 [kHz] to the discharge electrodes.

* * * * *